United States Patent
Battle et al.

(10) Patent No.: US 8,818,066 B2
(45) Date of Patent: Aug. 26, 2014

(54) GRID COMPUTING ON RADIOLOGY NETWORK

(75) Inventors: Xavier Battle, Knoxville, TN (US); Joseph Y. Fang, Barrington, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 238 days.

(21) Appl. No.: 13/604,954

(22) Filed: Sep. 6, 2012

(65) Prior Publication Data

US 2013/0058554 A1 Mar. 7, 2013

Related U.S. Application Data

(63) Continuation-in-part of application No. 10/880,112, filed on Jun. 29, 2004, now Pat. No. 8,285,826.

(51) Int. Cl.
| | |
|---|---|
| *G06K 9/00* | (2006.01) |
| *G06F 19/00* | (2011.01) |
| *G06F 15/173* | (2006.01) |
| *A61B 6/00* | (2006.01) |

(52) U.S. Cl.
CPC .............. *G06F 19/321* (2013.01); *A61B 6/563* (2013.01)
USPC .......................................... 382/131; 709/223

(58) Field of Classification Search
USPC ......... 382/128, 129, 130, 131, 132, 133, 134, 382/284; 709/218, 223, 227, 228, 230, 238, 709/241; 600/407; 128/920, 922
See application file for complete search history.

(56) References Cited

U.S. PATENT DOCUMENTS

| | | | | |
|---|---|---|---|---|
| 6,269,408 | B1 * | 7/2001 | Berliner | 719/324 |
| 6,587,598 | B1 * | 7/2003 | Devillers et al. | 382/284 |
| 7,218,766 | B2 * | 5/2007 | Eberhard et al. | 382/132 |
| 2004/0249314 | A1 | 12/2004 | Salla et al. | |
| 2005/0060202 | A1 | 3/2005 | Taylor et al. | |
| 2005/0213832 | A1 | 9/2005 | Schofield et al. | |
| 2006/0241968 | A1 | 10/2006 | Hollebeek | |
| 2007/0103984 | A1 | 5/2007 | Kavuri et al. | |
| 2008/0008401 | A1 | 1/2008 | Zhu et al. | |
| 2010/0280321 | A1 | 11/2010 | Modell | |

\* cited by examiner

*Primary Examiner* — Abolfazl Tabatabai
(74) *Attorney, Agent, or Firm* — Peter L. Kendall

(57) ABSTRACT

A grid computing system and method is provided for medical data processing. The grid computing system comprises a software infrastructure, and an imaging device capable of interfacing with the software infrastructure over a distributed electronic network. Also included is a plurality of CPUs capable of interfacing with the software infrastructure over the network. The performance of the plurality of CPUs is dependent on balancing load. A large medical dataset is split onto several processing nodes of the plurality of CPUs, respectively, such that performance and power is increased. In the grid computing method, a grid is limited to a nuclear medicine or radiology network. A tight and easy configuration management of computing nodes, and a tight load balancing between standardized nodes are provided. An existing network of CPUs is utilized, such that the greatest benefit is provided at the lowest cost.

16 Claims, 8 Drawing Sheets

GRID COMPUTING ON RADIOLOGY NETWORK

CROSS REFERENCE TO RELATED APPLICATIONS

This application is a Continuation-In-Part of U.S. Ser. No. 10/880,112, filed Jun. 29, 2004, now U.S. Pat. No. 8,285,826, the entirety of which is hereby incorporated by reference herein.

BACKGROUND OF THE INVENTION

1. Field of the Invention

The present invention relates generally to medical imaging and, more particularly, to a system and method of processing medical images.

2. Description of the Background Art

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, etc.

There are medical imaging processes of many types and for many different purposes, situations, or uses. They commonly share the ability to create an image of a bodily region of a patient, and can do so non-invasively. Examples of some common medical imaging types are nuclear imaging, magnetic resonance imaging (MRI), ultrasound, X-rays, tomography of various types, etc. Using these or other imaging types and associated machines, an image or series of images may be captured. Other devices may then be used to process the image in some fashion. Finally, a doctor or technician may read the image in order to provide a diagnosis.

The image may capture various details of the subject, which may include bones, organs, tissues, ducts, blood vessels, nerves, previous surgical artifacts such as implants or scar tissue, etc. The image or images may be two-dimensional (i.e., planar) or three-dimensional. In addition, the image capture may produce an image sequence or video that shows live operation, such as a functioning organ, for example. An imaging machine may capture an image, manipulate it, process it in some fashion in order to improve the image, display it to a doctor or technician, and store it for later use.

Computerized image processing generally requires that the image data conform to some sort of protocol, with the protocol being a set of rules and standards that ensure that the information may be efficiently communicated and manipulated among different apparatus. The Digital Imaging and Communications in Medicine (DICOM) standard provides a well-defined and accepted data format and interaction protocol for communicating a processing medical image data, and is incorporated herein by reference. The DICOM standard is available from the Radiological Society of North America, Oak Brook, Ill. 60523-2251.

The DICOM standard has become popular for medical imaging because it ensures that conforming machines can operate on image data communicated from other conforming machines. Machines that may employ the DICOM standard may be workstations, CT scanners, MR images, film digitizers, shared archives (storage devices), printers, and other devices that may be used to process and store image and patient data.

FIG. 1 shows a conventional medical imaging system 100. The medical imaging system 100 may include an imager 107 and imager controller 106 (they may be an integrated device), a patient database 110, an output device 115, a scanner 117, and one or more workstations 122. The imager 107 and imager controller 106 capture an image or images of a patient. The imager 107 may be, for example, a gamma ray camera, an X-ray imager, a magnetic resonance imager (MRI), an ultrasound imager, etc. The patient database 110 may store patient information (i.e., a plurality of records containing a name, vital parameters, a doctor, medical conditions, etc.), and imaging data. The output device 115 may be, for example, a printer, a computer monitor or other display screen, a film developer, etc. The scanner 117 may be a scanning device that digitizes an image. The workstations 122 may be used to access the patient database 110 in order to add or retrieve data. Patient information might also be stored in local databases on the processing workstations. In that case, the patient database 110 acts as a data repository for storage. The various components may be connected by a distributed electronic network 103, such as, for example, a local area network (LAN), a wide area network (WAN), a virtual private network (VPN), or the Internet. The individual components may therefore be located in separate rooms, floors, buildings, or even separate hospitals, clinics or institutions (such as research centers that are not hospitals).

Computerized image processing is well known in the art. However, the need for computing power is ever increasing. For example, recent developments in tomographic reconstruction processes require more and more computing power to more accurately model the physics of image formation. Current processing software memory and processing power requirements may already exceed the specifications of the most powerful computers currently available on the market. As an example, in the field of SPECT imaging, the OSEM 3D reconstruction algorithm currently requires several hours of processing time to process a 256-cube volume, and is therefore not usable in a clinical practice. The processing power requirement is projected to only increase as scanners produce more and more data as resolution and speed increase, and as interest grows in obtaining full resolution co-registered or fused images from different modalities, such as SPECT-CT, PET-CT, SPECT-MRI, etc. Accordingly, there exists a present need in the art to reduce overall radiological image processing time.

SUMMARY OF THE INVENTION

The present invention is provided to solve the above-mentioned problem. According to an aspect of the present invention, there is provided a grid computing system. The grid computing system comprises a software infrastructure, and an imaging device capable of interfacing with the software infrastructure over a distributed electronic network. Also included is a plurality of central processing unit (CPU) workstations capable of interfacing with the software infrastructure over the network. The performance of the plurality of CPUs is dependent on properly balancing load. A large dataset of medical images are split onto several processing nodes of the plurality of CPUs, respectively, such that performance and power is increased.

According to another aspect of the present invention, there is provided a method of grid computing. In the method of the present invention, a grid is limited to a nuclear medicine or radiology network. A tight and easy configuration management of computing nodes, and a tight load balancing between standardized nodes are provided. An existing network of central processing units (CPUs) is utilized, such that the greatest benefit is provided at the lowest cost.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

It is noted that in this disclosure and particularly in the claims and/or paragraphs, terms such as "comprises," "comprised," "comprising," and the like can have the meaning attributed to it in U.S. patent law; that is, they can mean "includes," "included," "including," "including, but not limited to" and the like, and allow for elements not explicitly recited. Terms such as "consisting essentially of" and "consists essentially of" have the meaning ascribed to them in U.S. patent law; that is, they allow for elements not explicitly recited, but exclude elements that are found in the prior art or that affect a basic or novel characteristic of the invention. These and other embodiments are disclosed or are apparent from and encompassed by, the following description. As used in this application, the terms "component" and "system" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

Furthermore, the detailed description describes various embodiments of the present invention for illustration purposes and embodiments of the present invention include the methods described and may be implemented using one or more apparatus, such as processing apparatus coupled to electronic media. Embodiments of the present invention may be stored on an electronic media (electronic memory, RAM, ROM, EEPROM) or programmed as computer code (e.g., source code, object code or any suitable programming language) to be executed by one or more processors operating in conjunction with one or more electronic storage media. This electronic storage media may include, for example a non-transitory electronic storage medium/media such as a register, or other electronic repository or electronic storage location for data that is capable of storing data represented in electronic form, such as bits, bytes, kilobytes, waveforms, electronic signals, digital format and other data types, formats and forms of data.

Embodiments of the present invention may be implemented using one or more processing devices, or processing modules. The processing devices, or modules, may be coupled such that portions of the processing and/or data manipulation may be performed at one or more processing devices and shared or transmitted between a plurality of processing devices.

Figure 1:
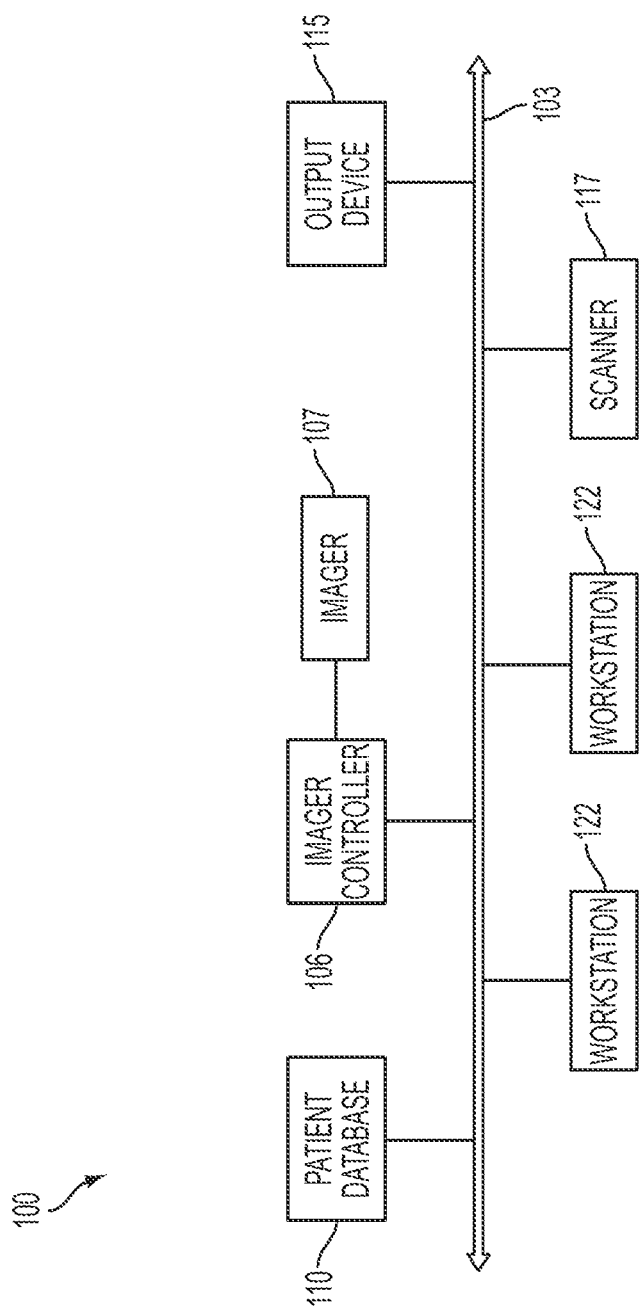
FIG. 1 is a conventional medical imaging system.
Figure 2:
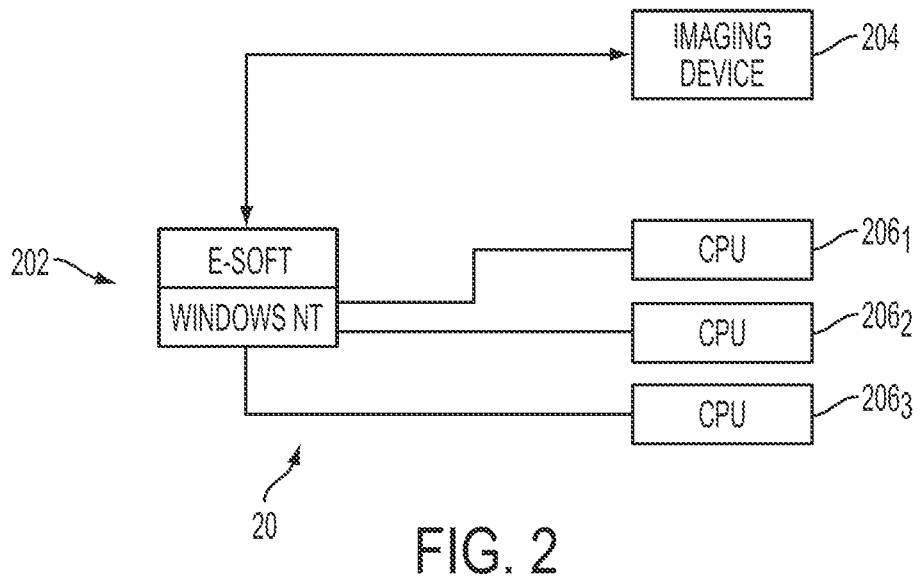
FIG. 2 shows the grid computing system according to an exemplary embodiment of the present invention.

As illustrated in FIG. 2, the grid computing system 20 comprises a master processing workstation 202, an imaging device 204, and a plurality of computing nodes $206_1$-$206_n$. In accordance with the principle of a computing "grid," each workstation is/can be both master and computing node. The imaging device 204 and the plurality of computing nodes $206_1$-$206_n$, interface with the master processing workstation 202 over a network such as, for example, a local area network (LAN), a wide area network (WAN), a virtual private network (VPN), the Internet, or the like.

According to one particular example embodiment of the invention, the master processing workstation 202 may be based on the universally accepted Windows $NT_7$ operating system with a graphical user interface (GUI) that is simple and intuitive. However, the invention is not restricted to any particular operating system or platform, but works on any platform or operation system.

Referring to FIG. 2, the imaging device 204 may be a combined scanning device, such as, for example, positron emission tomography/computed tomography (PET-CT), single photon emission computed tomography/computed tomography (SPECT-CT), or the like. It will be appreciated by those skilled in the art that the imaging device 204 also can be a single imaging device such as, for example, SPECT, planar imaging, or PET or MRI or Ultrasound or any other type of data collecting device.

The plurality of computing nodes $206_1$-$206_n$, can be clusters and networks of workstations interfacing with the master processing workstation 202 over the network, clusters and networks of personal computers interfacing with the master processing workstation 202 over the network, or a combination of clusters and networks of workstations and of personal computers interfacing with the master processing workstation 202 over the network. Accordingly, multimodality images can be viewed on the computing nodes $206_1$-$206_n$, alongside CT, MR, ultrasound, NM, angiography images, or the like. The computing nodes $206_1$-$206_n$, allow access to a universe of information and provide unlimited functionality.

Performance of the plurality of computing nodes $206_1$-$206_n$, is dependent on the ability to balance load, and maintain parallel processing software infrastructure (e.g., versions, updates, software, hardware obsolescence, etc.). In the parallel processing method of the present invention, a large medical dataset is split onto several processing nodes. The acceleration ratios obtained are usually equal to the number of computing nodes.

It is noted that the medical dataset is not limited to images. The benefit of more computing power allows one to consider processing raw information from the scanner before it is actually formatted into images, for example, list mode processing in nuclear medicine carries out processing on count data in the form of a sequential list of numerical values.

When demand processing is performed on the cluster of processing nodes $206_1$-$206_n$, significant and sustainable computer power improvement is achieved (e.g., maximum performance and reliability). Alternatively, when reconstruction load is spread on clusters and networks of workstations and personal computers $206_1$-$206_n$, good performance is achieved. Users such as research sites can mix the workstations and personal computers $206_1$-$206_n$ to achieve the highest demand of computing power.

Figure 3:
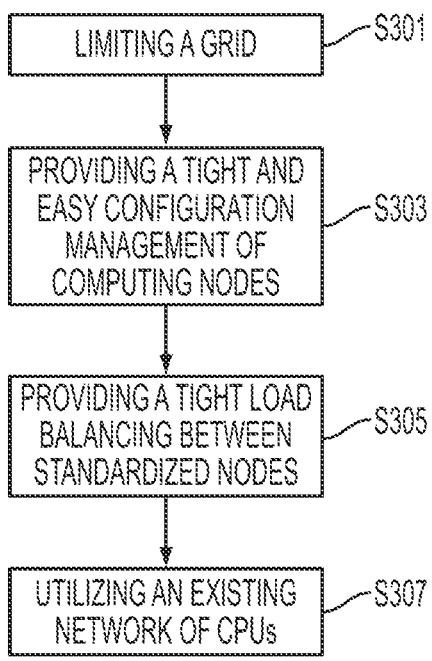
FIG. 3 is a flow chart of the method of grid computing according to an exemplary embodiment of the present invention.

FIG. 3 is a flow chart of a method of grid computing according to an exemplary embodiment of the present invention. In step S301, a network grid is limited to a nuclear medicine or radiology network. This has the beneficial effect of reserving the computing power for those applications that require the most intensive processing. In step S303, a tight and easy configuration management of computing nodes is provided, and a tight load balancing between standardized nodes is also provided (step S305). An existing network of central processing units (CPUs) is utilized in step S307, such that the greatest benefit is provided at the lowest cost (eq., cycles on idle machines are not wasted).

The grid computing system and method as described herein provide several benefits such as increased performance and power (e.g., maximum performance and reliability).

Next, referring to FIGS. 4A and 4B, another embodiment of the present invention will be described.

Figure 4A:
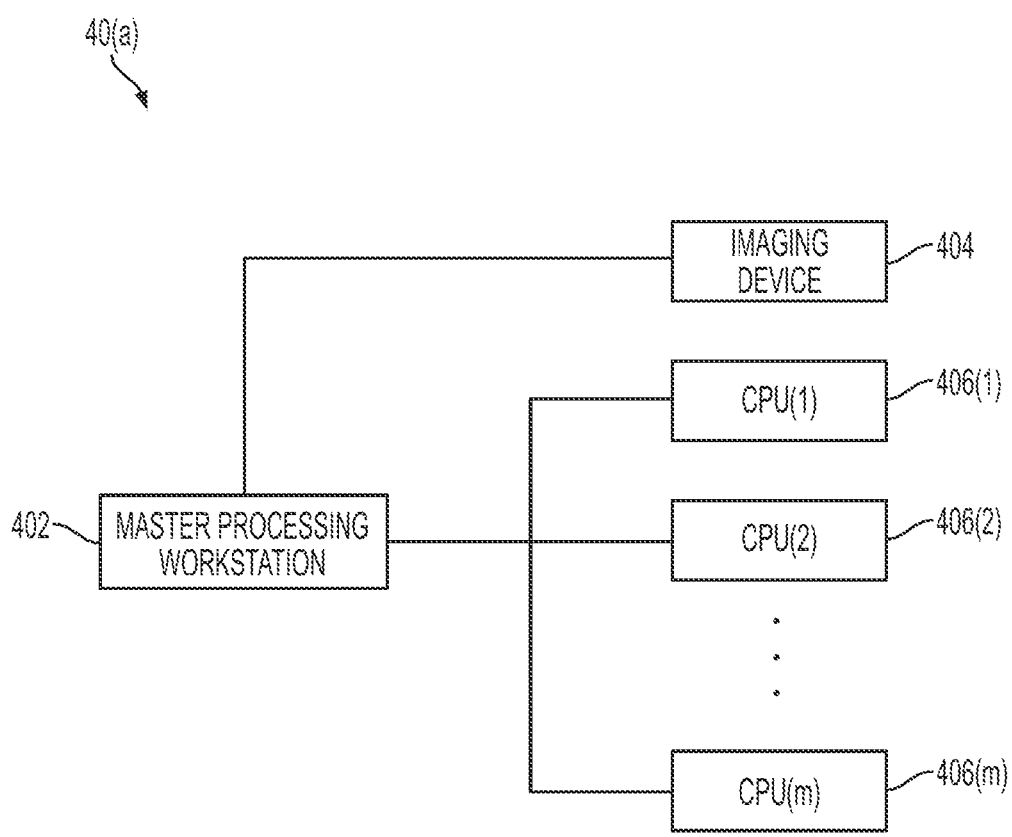
FIGS. 4A and 4B show examples of a gird computing system in which the number of computing nodes increases.

As illustrated in FIG. 4A, the grid computing system 40a comprises a master processing workstation 402, an imaging device 404, and a plurality of computing nodes 406(1), 406(2) . . . 406(m) (where "m" is any suitable number). After the medical image is captured by the imaging device 404, the master processing workstation 402 parses the medical image data into m subsets of image data, and transmits these m subsets of image data to the associated m computing nodes 406(1), 406(2) . . . 406(m), respectively. After data processing at each computing node 406(1), 406(2) . . . 406(m), subsets of processed data are transmitted back to the master processing workstation 402, at which the subsets of processed data are combined to generate three-dimensional medical image data representation. The detailed processing of the grid system will be described in relation to FIG. 5.

Figure 4B:
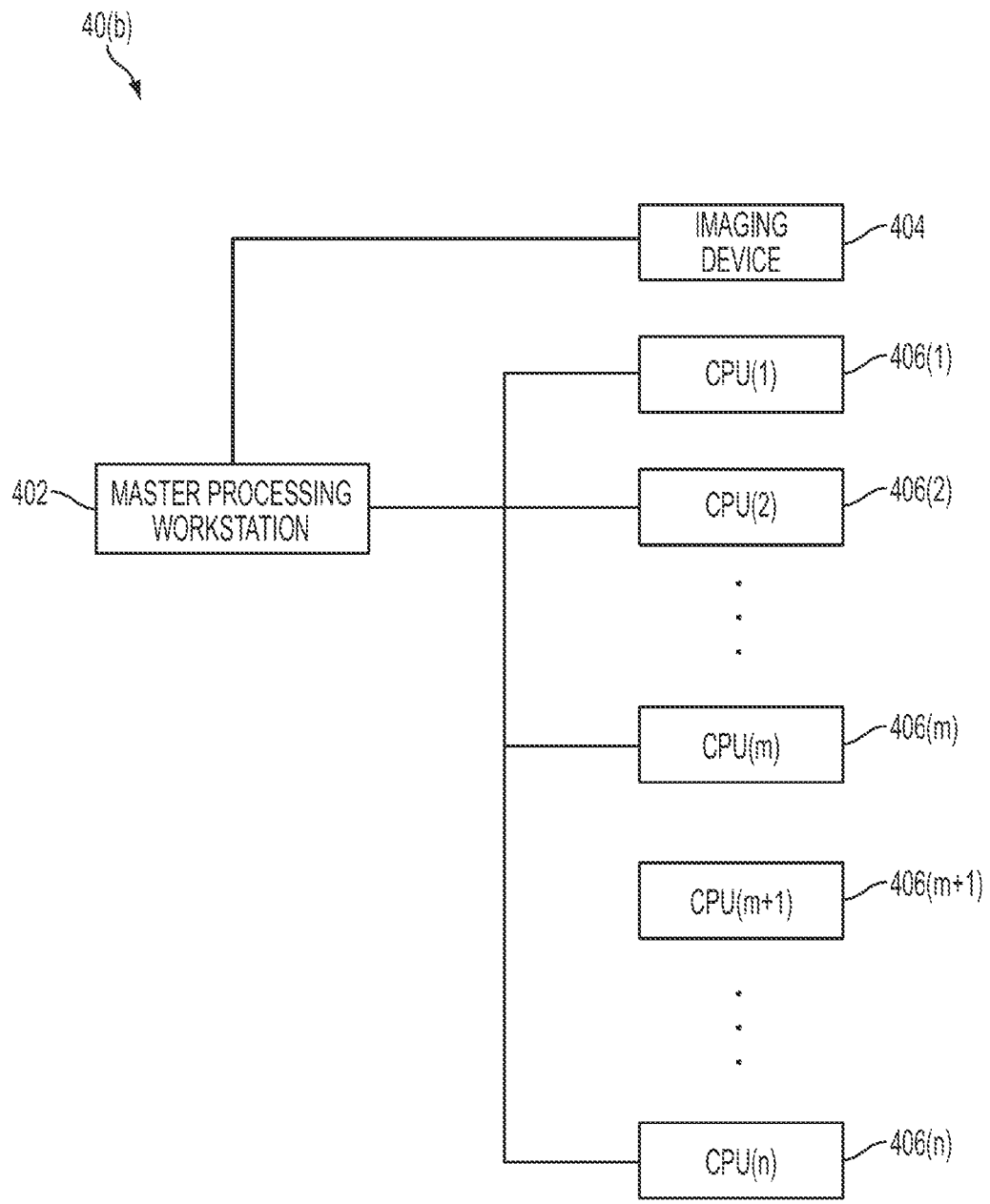

As illustrated in FIG. 4B, system 40b, when the grid computing system is updated by increasing the number of the computing nodes from m to n, besides the master processing workstation 402, the imaging device 404, and the plurality of computing nodes 406(1), 406(2) . . . 406(m), the updated grid computing system 40b further comprises a plurality of newly added computing nodes 406(m+1), 406(m+2) . . . 406(n) (where "n" is any suitable number no less than "m"). After the number of the computing nodes increases from "m" to "n", the master processing workstation 402 adapts itself to the new number "n" without reconfiguration, i.e., the master processing workstation 402 parses the medical image data into n subsets of split image data, and transmits these m subset of split image data to the associated n computing nodes 406(1), 406(2) . . . 406(n), respectively. In this case, when new workstations are added, for example, a new laboratory, nurses' station, reading room which has a particular number of computing nodes is added in the hospital, the overall performance of each processing may be increased, assuming that not all computers will be available at a particular time. Thus, as the number of processing computers grows, or increases, the number of potential processing modules for the grid system increase.

Furthermore, it is an embodiment of the present invention that in the grid computing system 40a or 40b shown in FIGS. 4A and 4B, when parts of the network, such as a particular number of the computing nodes, become unavailable for processing data (for example power outage), as long as there is still one node that is operational, the entire grid computing system will continue performing the data processing without termination, or interruption. Therefore, in accordance with the present invention, the grid computing system 40a or 40b approach is more resilient and adaptive than the conventionally used centralized approach.

In accordance with the present invention, the grid computing system 40a or 40b is adapted for use with a centralized processing server and serve "ready made" images to thin clients (client modules that do not perform any processing functions or operations). Thus, when compared with cloud computing, in which the cloud is typically a rented computing utility, in the present invention it is the hospital's own network of workstations, processing devices and personal computers (PCs) (i.e., the user may define the hospital's workstations and PCs as the computing nodes of the grid computing system).

Figure 5:
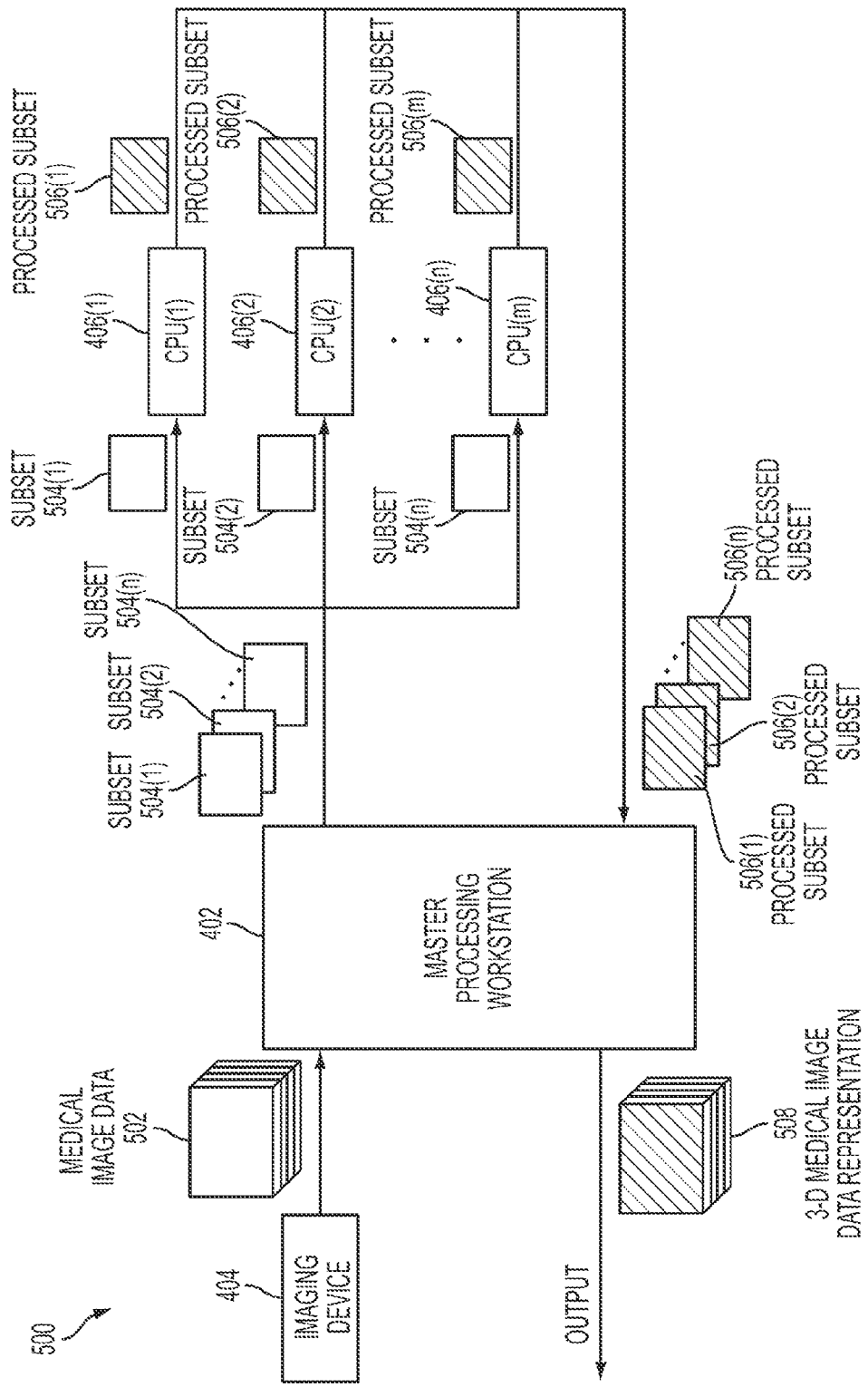
FIG. 5 shows a block diagram showing an example of processes of the grid computing system.

FIG. 5 illustrates a diagram 500 showing an example of processes of the grid computing system according to an embodiment of the present invention.

As shown in FIG. 5, medical image data 502 is captured by image device 404, and transmitted to master processing work station 402, where the medical image data 502 is parsed into data splices, or subsets 504(1), 504(2) . . . 504(n). These data splices, or subsets 504(1), 504(2) . . . 504(n) are transmitted to associated computing nodes 406(1), 406(2) . . . 406(n), (where "n" is any suitable number), respectively. For example, data splice, or subset 504(1) is transmitted to computing node 406(1), data splice, or subset 504(2) is transmitted to computing node 406(2) . . . and data splice, or subset 504(n) is transmitted to computing node 406(n). At each computing node, after predetermined image data processing, manipulation or operation is performed, the processed data subsets 506(1), 506(2) . . . 506(n) are output from the associated computing nodes 406(1), 406(2) . . . 406(n), respectively, and transmitted back to master processing work station 402. The predetermined image data processing includes processing the subset data to generate a three-dimensional (3-D) representation. The image processing may be any desired processing operations provided as instructions to the processing module.

At the master processing work station 402, the processed data subsets 506(1), 506(2) . . . 506(n) are combined according to their initial sequence to generate three dimensional data representation 508, which is output from the master processing workstation 402.

Figure 6:
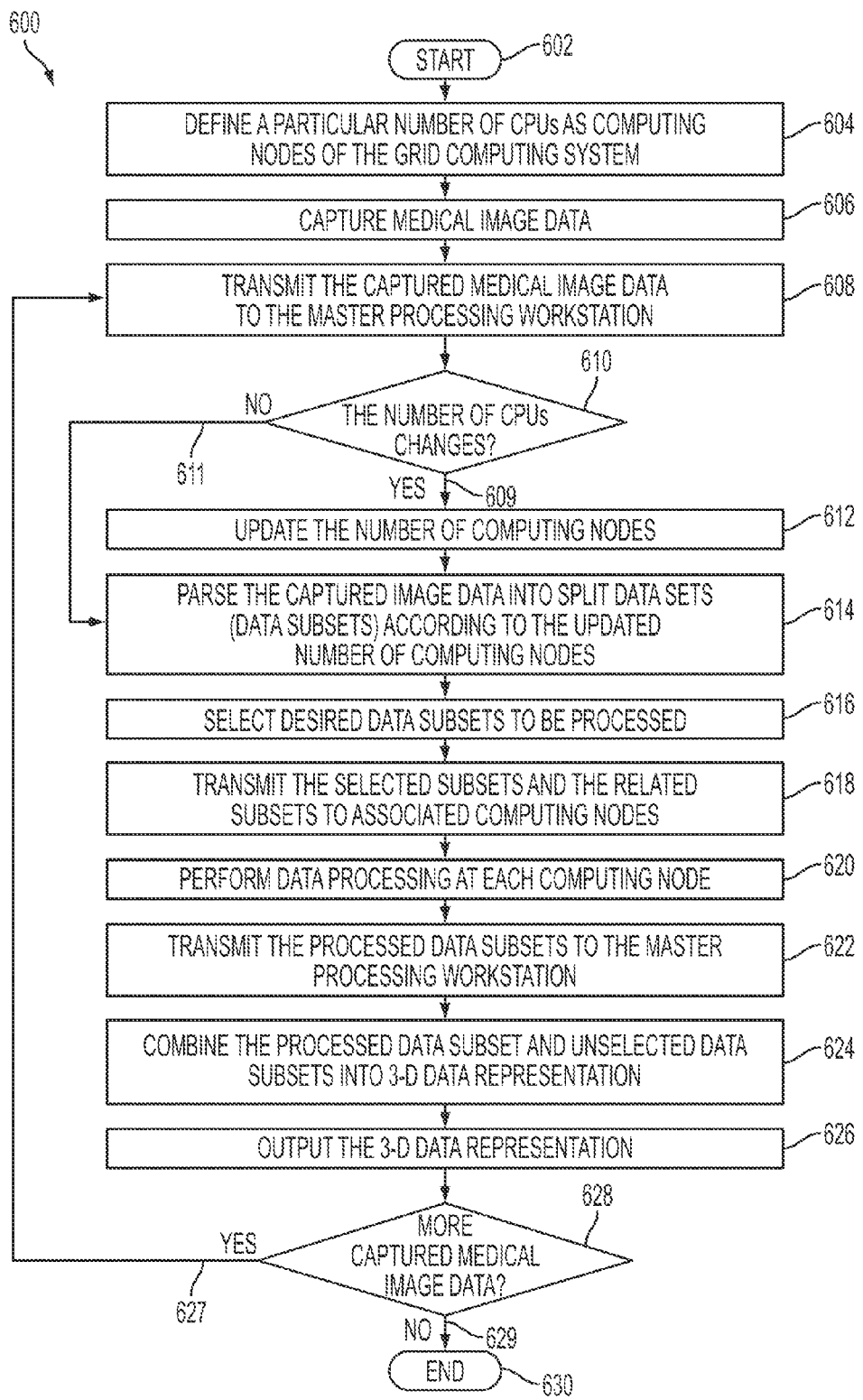
FIG. 6 shows an example of a series of steps of processes of the grid computing system.

FIG. 6 illustrates an example of a series of steps of processes of the grid computing system according to an embodiment of the present invention. The series of steps 600 may be stored on a non-transitory computer readable medium or media (e.g., RAM, ROM, EEPRPOM, DRAM or other memory, electronic storage device or registry) and may be executed by a processor or plurality of processors. The steps 600 may be computer code or other program code (e.g., source code) that may be compiled into object code. The code, stored on a medium and/or accessed, is a module, which may include electronic storage and/or processing functionality. The storage medium may be resident on the device (local) or accessed from a remote device (remote). The steps 600 are typically executed by a processor having adequate speed and processing capabilities. The execution may be at the client device and/or an associated server device. The steps 600 may be computer code or other program code (e.g., source code) that may be compiled into object code. The code, stored on a medium and/or accessed, is a module. The steps 600 may be stored on any one or more suitable modules described in relation to FIGS. 4A, 4B, 5, 7 and 8 herein.

Specifically, FIG. 6 shows that program code 600 begins with start step 602. In step 604 a particular number of CPUs, for example n CPUs, are defined as "n" (where "n" is any suitable number) computing nodes of the grid computing system by the user. In step 606, an imaging device (e.g., See FIG. 4, element 404) captures medical image data and the captured image data is transmitted to the master processing workstation (e.g., See FIG. 4, element 402), as shown in step 608.

In step 610 a determination is made whether the number of the computing nodes changes. If not, "no" line 611 leads to step 614. If more computing nodes are available to the grid computing system (i.e., the number of available processing nodes increases), or if some computing nodes in the system become unavailable (i.e., the number decreases), "yes" line 609 leads to step 612, in which the number of computing nodes is updated, and then in step 614 the captured image data is parsed into data subsets according to the number of available computing nodes. For example, if the number of the available computing nodes is "n", the captured image data may be parsed into n subsets of data, which are data subsets (e.g., See FIG. 5, elements 506(1), 506(2) . . . 506(n)).

In step 616, the data subsets which are desired to be processed may be selected and transmitted to the associated one or more available computing nodes. For example, among the n subsets of data, if the user only needs data subset (e.g., See FIG. 5, element 506(5)) to be processed, only three data subsets, including (i) the desired data subset (e.g., See FIG. 5, element 506(5)), (ii) data subset (e.g., See FIG. 5, element 506(4)) which is the data subset prior to the desired data subset (e.g., See FIG. 5, element 506(5)) in time sequence, and (iii) data subset (e.g., See FIG. 5, element 506(6)) which is the data subset following the desired data subset (e.g., See FIG. 5, element 506(5)) in time sequence, are required to be transmitted to the computing nodes, and other data subsets may not be transmitted. In this way, the grid computing system works more efficiently without transmitting unnecessary data.

In step 620, at each computing node, the data subset is processed according to the predetermined data processing, which may include manipulations, or execution of program code, and in step 622 the processed data subsets are transmitted from the computing nodes (e.g., See FIG. 4, element 406(1), 406(2) . . . 406(n)), respectively, to the master processing workstation (e.g., See FIG. 4, element 402).

In step 624, the processed data subsets and those data subsets not selected in step 616 (if any) may be combined based on the time sequence of the data subsets to generate three-dimensional medical data representation (e.g., See FIG. 5, element 508). The generated three-dimensional (3-D) data representation (e.g., See FIG. 5, element 508) may be output from the master processing workstation (e.g., See FIG. 4, element 402), as shown in step 626.

In step 628 a determination is made whether there is more captured image data to be processed. If so, "yes" line 627 leads back to step 608. Otherwise, if there is no more captured image data, "no" line 627 leads to end step 630.

In accordance with the present invention, alternatively, in step 614, the captured medical data may be parsed into any number of subsets, instead of the same number equal to the number of the computing nodes. For example, the whole captured medical data set may be transmitted to each of the computing node without being parsed. Another example, for a computing system with three computing nodes, under the control of the master processing workstation, one-third (⅓) of the whole medical data set may be transmitted to the first computing node, and the remaining portion (two-thirds) of the whole medical data set may be transmitted to the second computing node, so that there will be no data transmitted to the third computing node.

In accordance with the present invention, at each computing node, based on the different data processing capacity at each computing node, the subset of medical data may be processed at different data processing rate. Therefore, the master processing workstation (see FIG. 4, element 402) may get feedback information indicating the data processing rate of the computing node from each computing node, respectively. Based on the data processing rate of each computing node, the master processing workstation may assign different amount of medical data to these computing nodes.

Figure 7:
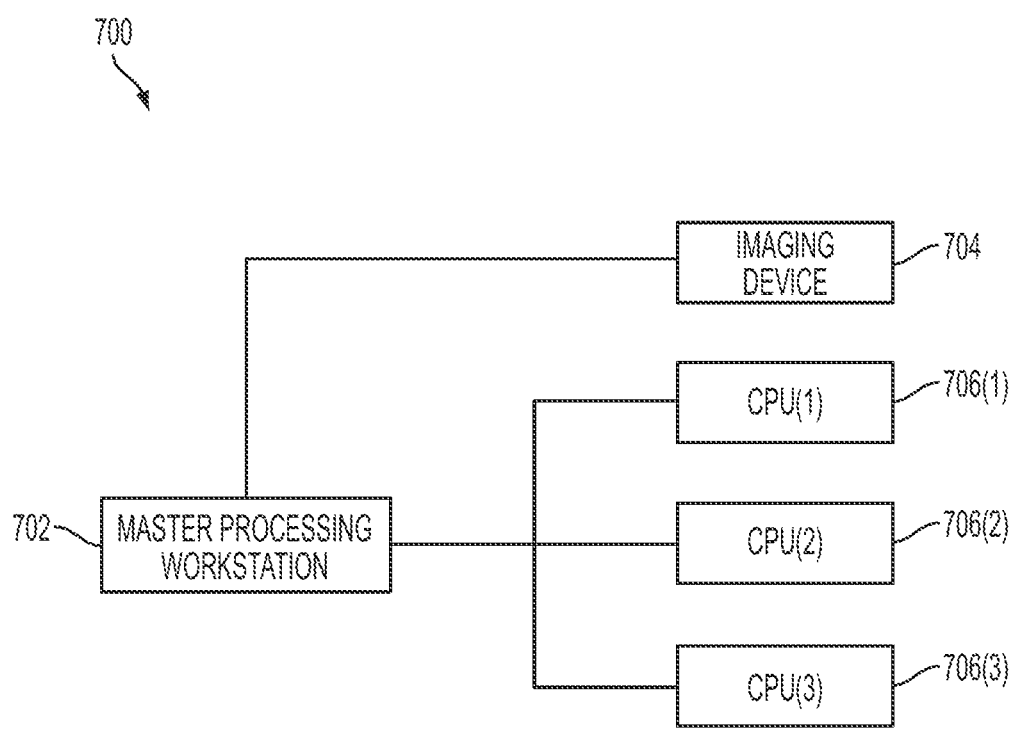
FIG. 7 shows an example of a grid computing system with four computing nodes.

FIG. 7 shows an example of a grid computing system with four computing nodes. The computing system shown in FIG. 7 may be implemented using one or more processing devices, or processing modules or facilities. The processing devices, or modules, or facilities, may be coupled such that portions of the processing and/or data manipulation may be performed at one or more processing devices and shared or transmitted between a plurality of processing devices.

For example, as shown in FIG. 7, if the data processing rate, or capacity, of a first computing node 706(1) is twice that of the data processing rate, or capacity, of the second computing node 706(2) and the third computing node 706(3), the master processing workstation 702 may assign one-half of the whole medical data set to the first computing node 706(1), and assign one-fourth of the whole medical data set to the second computing node 706(2) and the third computing node 706(3), respectively. Another example is that if data processing rate of a particular computing code is much lower than other computing nodes, the master processing workstation may stop transmitting data to this particular computing node, and adjust the number of the subsets of data to be transmitted to other computing nodes. Therefore, the data processing rate of the whole system may increase.

In accordance with the present invention, the master processing workstation and the computing nodes, may be any device with a processor that might be connected to the computing system, for example, personal computer, cell phone, PDA, television, video game device and the like.

In accordance with the present invention, the original captured medical data may be not only two dimensional image data obtained by any image obtaining unit, but also one dimensional ultrasound data.

Furthermore, in accordance with the present invention, the grid computing system adapts itself to the number of the computing nodes, so the medical image data may be processed more efficiently. For example, when the medical image data is obtained by the imaging device (e.g., See FIG. 4, element 404) at a predetermined frequency, the three dimensional data representation may be generated to show a dynamic operation of a functioning organ of a living body. Moreover, if the three dimensional data representation of the dynamic operation of the functioning organ is generated at regular intervals, such as every month or every year, the operation of the functioning organ may be monitored and stored for the hospital's record.

Figure 8:
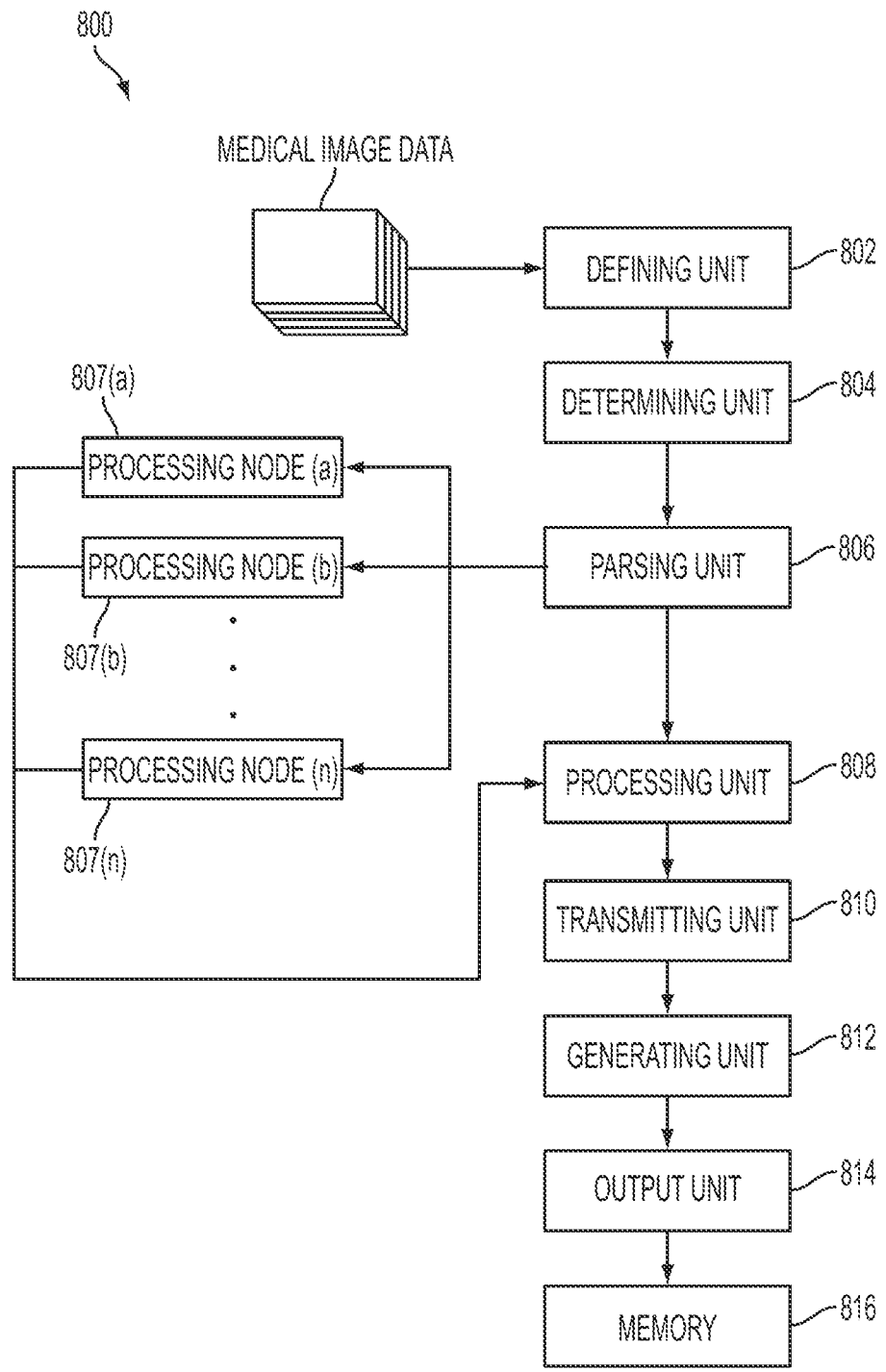
FIG. 8 shows a block diagram of modules and components according to another embodiment of the present invention.

FIG. 8 shows a block diagram 800 of modules and components according to another embodiment of the present invention. Embodiments FIG. 8 may be implemented using one or more processing devices, or processing modules, or facilities. The processing devices, or modules, or facilities, may be coupled such that portions of the processing and/or data manipulation may be performed at one or more processing devices, modules or facilities and shared or transmitted between a plurality of processing devices. FIG. 8 includes medical image data, a defining unit 802, a determining unit 804, a parsing unit 806, processing nodes 807(*a*) . . . (*n*) (where "n" is any suitable number), processing unit 808, transmitting unit 810, generating unit 812, output unit 814 and memory unit 816.

The data, which is typically medical image data that is in a particular format, such as pixels, two-dimensional, one-dimensional or other data obtained from an imaging process of a patient. The image data is accessed by defining unit 802. The defining unit 802 defines a plurality of computing nodes that are available to perform processing operations, manipulations and/or functions. The defined computing nodes may be defined, or identified by a user, or program code by sending an API (Application Program Interface), or "ping" to possible computing nodes as a status check to determine all possible computing nodes that may be available to perform processing operations.

The determination unit 804 is used to determine which of the plurality of computing nodes is available for performing processing. Since all possible nodes that are identified by the defining unit may not be available to actually perform proceeding functionality, the determining unit 804 can select those nodes that respond to the API or ping, as actually receptive to processing requests.

The parsing unit 806 is used for parsing the medical data into a plurality of medical data subsets. The number of the medical data subsets being based on the number of the available computing nodes, or processing nodes, 807(*a*) . . . (*n*). The number of subsets may be a function of the nodes (generally 807) processing power, or capability, or speed. Indeed one embodiment of the present invention is that the number of subsets is equal to the number of processing nodes 807. Alternatively, each of the processing nodes 807 may receive a disproportionate amount of subsets based on the processing capability of each node 807. Specifically, some node 807 that are available may not receive any subsets, while other ones of the nodes 807 may receive a plurality of subsets.

The processing unit 808 is used for processing, organizing, compiling and/or re-assembling each subset received from an associated one of the plurality of computing nodes 807. Alternatively, the processing unit 808 may perform actual processing functionality of one or more subsets of data itself. This processing unit 808 is typically used as a managing, or control processing unit, to control the final processing of the processed data received from nodes 807.

The transmitting unit 810 is used to transmit the processed medical data subsets to a master node, which may be processing unit 808, or other node.

The generating unit 812 is used for generating a representation of the image data at the master node by combining the processed medical data subsets. The representation may be, for example, a three-dimensional (3D) representation, a voxel representation, a color representation or model of the image data.

The output unit 814 is used to output the representation, This unit 814 may be a computer screen, printer or other suitable output device to display or output the representation.

The memory 816 is also available to store the representation output from output module 816.

While a preferred embodiment of the present invention has been described above, it should be understood that it has been presented by way of example only, and not limitation. Thus, the breadth and scope of the present invention should not be limited by the above described exemplary embodiment.

Obviously, numerous modifications and variations of the present invention are possible in light of the above teachings. It is therefore to be understood that the invention may be practiced otherwise than as specifically described herein.

The invention claimed is:

1. A method of processing medical data by a computing system, comprising steps of:
   defining a plurality of computing nodes as computing nodes of the computing system;
   determining which of the plurality of computing nodes is available for performing processing;
   parsing medical data into a plurality of medical data subsets, the number of the medical data subsets based on the number of the available computing nodes;
   processing each medical data subset at an associated one of the plurality of computing nodes;
   transmitting the processed medical data subsets to a master node; and
   generating a three dimensional data representation at the master node by combining the processed medical data subsets.

2. The method of processing medical data according to claim 1, further comprising step of:
   when the number of the available computing nodes changes, adjusting the number of the plurality of medical data subsets independent of reconfiguration; and
   when data processing rate of a particular computing node is lower than a predetermined threshold, terminating transmitting medical data subsets to the particular computing node and adjusting the number of medical data subsets independent of reconfiguration.

3. The method of processing medical data according to claim 1, wherein medical data set is a two-dimensional data representation.

4. The method of processing medical data according to claim 1, wherein when a particular medical data subset of the plurality of medical data subsets is requested to be processed at the associated computing node, a medical data subset prior to the particular medical data subset and a medical data subset following the particular medical data subset, are transmitted to the associated computing nodes, respectively, independent of transmission of other medical data subsets.

5. The method of processing medical data according to claim 1, further comprising steps of:
   generating a plurality of three dimensional data representations at a plurality of different time points on temporal dimension; and
   comparing the plurality of three dimensional data representations at the plurality of different time points.

6. The method of processing medical data according to claim 1, wherein
   the three dimensional data representation is a dynamic data representation.

7. The method of processing medical data according to claim 1, wherein the medical data is captured by an imaging device, which is a combined imaging apparatus having at least two different imaging modalities.

8. The method of processing medical data according to claim 7, wherein said combined imaging apparatus is a positron emission tomography/computed tomography (PET-CT) imaging device.

9. The method of processing medical data according to claim 7, wherein said combined imaging apparatus is a single photon emission computed tomography/computed tomography (SPECT-CT) imaging device.

10. The method of processing medical data according to claim 1, wherein said imaging device is a single scanning device.

11. The method of processing medical data according to claim 10, wherein said single scanning device is a SPECT, PET, single photon planar, or X-ray imaging devices.

12. The method of processing medical data according to claim 1, wherein said computing nodes of the computing system consists of clusters and networks of workstations.

13. The method of processing medical data according to claim 1, wherein computing nodes of the computing system consists of clusters and networks of personal computers.

14. The method of processing medical data according to claim 1, wherein the parsing step further comprises:
parsing the medical data subsets so that the number of the medical data subsets is equal to the number of the available computing nodes.

15. A computing system for processing medical data, comprising:
a defining unit for defining a plurality of computing nodes as computing nodes of the computing system;
a determination unit for determining which of the plurality of computing nodes is available for performing processing;
a parsing unit for parsing medical data into a plurality of medical data subsets, the number of the medical data subsets being based on the number of the available computing nodes;
a processing unit for processing each medical data subset at an associated one of the plurality of computing nodes;
a transmitting unit for transmitting the processed medical data subsets to a master node; and
a generating unit for generating a three dimensional data representation at the master node by combining the processed medical data subsets.

16. The system according to claim 15, wherein the parsing unit parses the medical data subsets so that the number of the medical data subsets is equal to the number of the available computing nodes.

* * * * *